United States Patent Office

Re. 27,332
Reissued Apr. 11, 1972

27,332

PERFUME COMPOSITIONS CONTAINING GERANONITRILE, CINNAMYL NITRILE OR 2-NONENYL NITRILE

Willard T. Somerville, Monmouth, N.J., and Edward J. Shuster, Brooklyn, N.Y., assignors to International Flavors & Fragrances Inc., New York, N.Y.

No Drawing. Original No. 3,325,369, dated June 13, 1967, Ser. No. 335,071, Mar. 26, 1964, which is a continuation-in-part of Ser. No. 277,695, May 3, 1963. Application for reissue Mar. 23, 1970, Ser. No. 22,072
Int. Cl. A61k 7/00
U.S. Cl. 252—522 6 Claims

Matter enclosed in heavy brackets [ ] appears in the original patent but forms no part of this reissue specification; matter printed in italics indicates the additions made by reissue.

*ABSTRACT OF THE DISCLOSURE*

*Compositions containing geranonitrile to impart thereto a citrusy lemon-like odor, but substantially free from discoloration and odor degradation. Such compositions may include soaps or detergents.*

This invention relates to perfumes, and more particularly to perfume mixtures for use in soaps, cosmetics, space deodorants and the like.

Soaps and similar compositions are generally blended with perfume mixtures containing at least one ingredient selected to impart a pleasing odor. [Often $\alpha,\beta$-unsaturated aldehydes are used to impart the desired odor.] It has been found that one of the most pleasant and acceptable odors is the fresh, citrusy, lemon-like odor which is obtained by blending citral either alone or as an ingredient in a perfume mixture in soaps and like compositions. [Other desirable odors are imparted with other aldehydes such as cinnamaldehyde and 2-nonenyl aldehyde.]

This application is a continuation-in-part of our earlier application Ser. No. 277,695, filed May 3, 1963, now abandoned.

We have found that citral [and other such aldehydes have poor stability. Thus citral, when] incorporated in various compositions either alone or in a mixture discolors on standing and its odor becomes degraded. The principal object of [the] our invention, accordingly, is to find a substitute for [$\alpha,\beta$-unsaturated aldehydes such as citral] which, while possessing the desirable characteristics of [the aldehydes] *citral* can be blended in the compositions mentioned either alone or as part of a perfume mixture without substantial deterioration with respect to odor, color or other desirable qualities.

We have found in accordance with our invention that geranonitrile, which is a known substance having the formula

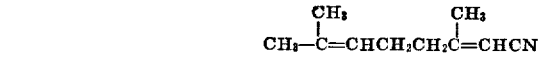

has the desired citrusy, lemon-like odor of citral and when blended in compositions including soap, detergents, cosmetics, space deodorants and the like, shows substantially no discoloration or degradation of odor on storage for long periods of time.

[We have also discovered that cinnamonitrile has the quality characteristic of cinnamaldehyde, but with a special green top note. In soap and other compositions, it is decidedly superior to the corresponding aldehyde in both color and odor stability.]

[In addition, we have found that 2-nonenyl nitrile has the cinnamon-like characteristics of the corresponding aldehyde. The fragrance quality of the latter, however, disappears so rapidly in all media that it is worthless as a perfume. The nitrile, however, is stable and retains its fragrance characteristics as a perfume and in perfume mixtures when used in compositions such as soaps, powders and others as referred to above.]

The invention comprises the novel products, the specific embodiments of which are described hereinafter by way of example and in accordance with which we now prefer to practice the invention.

As produced by us geranonitrile contains approximately one-third cis form and two-thirds trans form by weight. This isomer mixture is substantially similar in odor properties with citral, and we prefer to use it either alone or in mixtures in compositions such as those mentioned. Similar effects may be obtained if the isomer ratio is not exactly adhered to.

[Cinnamonitrile and 2-nonenyl nitrile are prepared in accordance with standard procedures for example from the corresponding oxime and may be obtained either as pure isomers or as mixtures of cis and trans forms. Whether utilized as isomers or as mixtures, the compounds are remarkably stable in odor and color.]

We have found in accordance with our invention that [the aforesaid nitriles] *geranonitrile* may be utilized alone, as above stated, for example in sachets for use in bureaus and in closets, and in other ways that compositions are normally employed. [They] *Geranonitrile* may also be employed alone or in mixtures in detergents, cosmetics, soaps, space deodorants and other formulations.

In this connection, we have found unexpectedly that geranonitrile may be combined with soaps which have an alkaline reaction in use, or in some detergents which have an acid reaction, without changing its stability with respect to color or odor. Compositions of this sort which include geranonitrile have an extremely long shelf like, while citral, when included in the same compositions, has a relatively short shelf life, as shown by the test below. [Similar results are obtained with the nitriles mentioned above and similar nitriles.]

The following are examples of the perfume mixtures and soap and other formulations as we now prefer to produce them. It is to be understood that these compositions are preferred examples and the invention is not to be considered as restricted thereto except as indicated in the appended claims.

Example I.—Preparation of soap composition with geranonitrile

A total of 100 grams of soap chips were mixed with one gram of the perfume mixture given below until a substantially homogeneous composition was obtained. Another soap composition was identically prepared except that the geranonitrile of the perfume mixture was replaced with three times the amount of citral. Both soap compositions mainfested a characteristic lemon-like odor despite the lesser amount of geranonitrile employed.

The perfume mixture consisted of the following ingredients in the parts by weight indicated:

| | |
|---|---|
| Geranium bourbon | 175 |
| Citronellol | 150 |
| Geraniol | 100 |
| Phenyl ethyl alcohol | 90 |
| Amyl cinnamic aldehyde | 200 |
| Cyclamal | 20 |
| Lyral [1] | 100 |
| Tetrahydro linalool | 37.5 |
| Tetrahydro myrcenol | 37.5 |
| Linalool | 75 |
| Citronellyl acetate | 125 |
| Phenyl ethyl acetate | 5 |
| Phenyl acetaldehyde dimethyl acetal | 10 |
| Cinnamic alcohol | 35 |
| Terpineol | 100 |
| Linalyl acetate | 25 |
| Musk ketone | 10 |
| Indole | 10 |
| Geranonitrile | 10 |

[1] Lyral is the registered trademark of International Flavors & Fragrances, Inc. for 4-(4-methyl, 4-hydroxy amyl)$\Delta^3$-cyclohexene carboxyaldehyde.

Example II.—Testing of soaps containing geranonitrile

Soap samples were prepared in accordance with the procedure of Example I. One group of samples contained 0.33% by weight of geranonitrile, the other 1% by weight of citral. Samples from each group were kept in closed containers in an oven at 140° F. for five days, after which they were compared with duplicate samples kept in closed containers at room temperature. In all cases, soaps containing citral were discolored. The odor of citral was already in the process of degradation. In contrast, the soaps containing geranonitrile were unchanged both in color and odor.

Example III.—Preparation of detergent compositions containing geranonitrile

A total of 100 grams of a detergent were mixed with 0.15 gram of the perfume mixture given below until a substantially homogeneous composition was obtained. Other detergent compositions were similarly prepared except that the geranonitrile was replaced with three times the amount of citral. Both compositions manifested a characteristic lemon-like odor of substantially equal strength despite the lesser amount of geranonitrile used.

The compositions were identically tested in accordance with the procedure described in Example II with the same results.

The perfume mixture used in preparing the detergents of this example consisted of the following ingredients in parts by weight indicated:

| | |
|---|---|
| Decyl aldehyde, 10% solution in diethyl phthalate | 4 |
| Terpinyl acetate | 100 |
| Terpineol | 40 |
| Linalyl acetate | 100 |
| Orange oil | 350 |
| Geranyl acetate | 100 |
| Geraniol | 35 |
| Coumarin | 2 |
| Geranonitrile | 3.5 |

Example IV.—Preparation of cosmetic powder composition containing geranonitrile

A cosmetic powder was prepared by mixing 100 grams of powder with 0.25 gram of geranonitrile in a ball mill. A second cosmetic powder was similarly prepared except that the geranonitrile was replaced with citral.

These cosmetic powders were oven tested as described in Example II at 100° F. for two weeks and it was observed that the powder containing the citral was discolored and its odor completely degraded, whereas the powder containing the geranonitrile was substantially unchanged in both color and odor.

[*Example V.—Testing of soap containing cinnamonitrile*]

[Test soap bases were prepared using in the one case one part of cinnamaldehyde for 100 parts of soap and in the other, one part cinnamonitrile for 100 parts of soap. The bars were tested in accordance with the procedure of Example II. It was found that in all cases the soap bars containing the aldehyde had discolored from white to yellow, and that there was an odor change and loss of strength of odor. The nitrile soap showed substantially no change in odor or color.]

[*Example VI.—Toilet soap composition with a perfume composition containing cinnamonitrile*]

[A perfume mixture containing the following ingredients in the parts by weight indicated was prepared:]

| | |
|---|---|
| [Musk ambrette | 4 |
| Coumarin | 20 |
| Geraniol | 12 |
| Eugenol | 24 |
| Cinnamic aldehyde or cinnamo nitrile | 24 |
| Methyl diphenyl ether | 24 |
| Bois de Rose Oil | 12 |
| Lavender spike | 34 |
| Rosemary tunisian | 36 |
| | 190] |

[Toilet soap bars were prepared and tested as in Example V. It was found that the aldehyde caused distinct yellowing of the soap bars and that the soap bars containing the nitrile remained white. Moreover, the bars containing the nitrile retained their original fragrance and odor balance whereas the odor balance was noticeably altered in the accelerated tests of toilet soap bars containing the aldehyde.]

[*Example VII.—Liquid detergent containing cinnamonitrile*]

[Concentrated liquid detergents samples containing, in the one case 0.2% by weight of cinnamonitrile and in the other 0.2% by weight of cinnamaldehyde were held at room temperature for ten days and compared with one another. At the end of this period an examination showed that the nitrile imparted a more powerful cassia note than the aldehyde, and that with the nitrile there was no change from the water white color of the original unperfumed liquid detergent base, while the aldehyde containing sample had changed to a lemon yellow color.]

[The detergent samples were further tested under use conditions by dissolving 0.5 gram of the perfumed detergents in separate 200 gram portions of warm water. When each was compared with freshly prepared samples of detergent the detergent containing the aldehyde in water exhibited evidence of degradation by change of the characteristic odor and loss of such odor, whereas the comparable nitrile-containing composition retained its full strong cinnamon-like odor, without loss of color, whereas the aldehyde containing composition exhibited a yellowish discoloration.]

[*Example VIII.—Powder detergent containing cinnamonitrile*]

[A comparison experiment was carried out in which detergent base powder samples containing 0.2 gram of cinnamaldehyde or 0.2 gram of cinnamonitrile per 100 grams of unperfumed detergent base powder were thoroughly mixed in a high speed-rotary roller blender. The samples were examined after 10 days storage in closed glass containers at room temperature. It was found that the odor of the aldehyde had lost its characteristics very rapidly, and that the powder has acquired a yellowish cast. The sample containing the nitrile retained its typical cinnamon note in full volume, and there was no change in color.]

[*Example IX.—Cosmetic powder containing cinnamonitrile*]

[A comparison experiment was carried out in which cosmetic talcum powder samples containing one gram of cinnamaldehyde or one gram of cinnamonitrile per 100 grams of unperfumed talcum powder were thoroughly mixed in a high speed rotary blender. The samples were stored in closed glass containers in an oven for one week at 100° F. In this medium the aldehyde note was completely altered and the talcum powder acquired a pale, ivory tint, whereas the nitrile retained its typical note with no discoloration of the powder base.]

[*Example X.—Cosmetic powder containing trans-2-nonenyl nitrile*]

[Separate mixtures, used as described in the following paragraph, were prepared containing one part trans-2-nonenyl nitrile in 1,000 parts of methyl ionone and one part trans-2-nonenal in 1,000 parts of the same substance.]

[Comparison experiments were carried out, in which 1% by weight of each mixture was incorporated in cosmetic talcum powder. The cosmetic compositions were tested in the same manner as the previous example, and it was found that there was a complete loss of the aldehyde aroma, whereas in the case of the nitrile the waxy, plant-like odor persisted at the end of the test period.]

[*Example XI.—Soap bars containing trans-2-nonenyl nitrile*]

[Separate mixtures were prepared containing one part trans-2-nonenyl nitrile in 1,000 parts para tertiary amyl cyclohexanone and one part trans-2-nonenal in 1,000 parts of the same substance.]

[These mixtures were incorporated into chips, at 1% by weight, mixed and plodded into bars. Some bars containing each perfume mixture were held at room temperature in closed containers for seven days. Other bars containing each mixture were held in closed containers in an oven at 140° F. for the same length of time. It was found that with the aldehyde, even with the samples held at room temperature, there was a noticeable loss of aroma. In the accelerated tests at 140° F. the loss was practically complete. With the nitrile containing samples, in both cases the original strength and balancing effect continued undiminished.]

[The same tests as above were carried out using 0.1% mixtures of said aldehyde and said nitrile in methyl ionone. The methyl ionone blend with the aldehyde was not much different than methyl ionone alone at the conclusion of the tests. The sample with said nitrile, on the other hand, maintained an unaltered floral and waxy note over the normal woody character of the methyl ionone.]

[The same tests were carried out using 0.1% mixtures of said aldehyde and said nitrile in diethyl phthalate. Aldehyde-containing soap bars held at 140° F. for only three days showed a marked fatty odor followed by progressive disappearance, until at the end of seven days the soap bars were almost devoid of starting odor. The said nitrile-containing soaps under the same circumstances retained the typical floral and waxy aroma.]

The use of [nitriles] *geranonitrile* in cosmetic powders is an especially rigorous test of [their] *its* stability, since in powders, degradation due to oxidation is accelerated because of the enormous surface area of the powder.

In the standard age acceleration tests used in the above examples a temperature of 110° F. for one week is equivalent to six months at ordinary temperature.

The amount of [nitrile] *geranonitrile* which will be effective in our compositions depends upon many factors, including [for example, the selected nitrile] the other ingredients present, their amounts and the effects which are desired. We have found that perfume mixtures containing as little as 0.02% by weight of [nitrile] *geranonitrile* or even less may be usefully employed. For certain mixtures as much as 12% by weight or even higher is useful. When these perfume mixtures are used in soaps and other products the amount is the same as is generally employed with ordinary perfume mixtures, i.e., from about 1% to about 3% by weight. Thus, as little as 0.0002% by weight of [the selected nitrile] *geranonitrile* may be employed to impart desirable aroma characteristics to soaps, cosmetics and other products.

While the description of our invention has been given in terms of what are presently considered the preferred embodiments, it will be obvious to those skilled in the art that various changes and modifications can be made therein without departing from the spirit and scope of the invention. It is the intention therefore, that the appended claims cover all such changes and modifications as fall within the spirit and scope of the invention.

In each of the above examples:

The "soap base" and "soap chips" used consisted of unperfumed sodium base toilet soap made from tallow and coconut oil.

The substance referred to as "detergent powder" was a powder obtained from Lever Bros. Co. being sold under the trademark "Rinso."

The substance referred to as "liquid detergent" was a product manufactured by Ultra Chemical Co., known as P–87 Liquid Detergent Base.

What is claimed is:

1. A perfume mixture containing an effective amount [of a nitrile selected from the group consisting] of geranonitrile [cinnamyl nitrile, 2-nonenyl nitrile and mixtures thereof] characterized by substantial freedom from discoloration and odor degradation on storage.

2. A composition comprising a soap together with a perfume mixture containing an effective amount [of a nitrile selected from the group consisting] of geranonitrile [cinnamyl nitrile, 2-nonenyl nitrile and mixtures thereof] characterized by substantial freedom from discoloration and odor degradation on storage.

3. A composition comprising a detergent together with a perfume mixture containing an effective amount of [a nitrile selected from the group consisting of] geranonitrile, [cinnamyl nitrile, 2-nonenyl nitrile and mixtures thereof] characterized by substantial freedom from discoloration and odor degradation on storage.

4. A composition comprising a cosmetic together with a perfume mixture containing an effective amount of [a nitrile selected from the group consisting of] geranonitrile [cinnamyl nitrile, 2-nonenyl nitrile and mixtures thereof] characterized by substantial freedom from discoloration and odor degradation on storage.

5. A composition comprising a space deodorant together with a perfume mixture containing an effective amount of [a nitrile selected from the group consisting of] geranonitrile [cinnamyl nitrile, 2-nonenyl nitrile and mixtures thereof] characterized by substantial freedom from discoloration and odor degradation on storage.

[6. A perfume consisting of a mixture of cis and trans isomers of geranonitrile having a citrusy lemon-like odor substantially identical with that of citral but substantially free from discoloration and odor degradation.]

*7. A perfume mixture as defined in claim 1, wherein said geranonitrile consists of a mixture of cis and trans isomers of geranonitrile.*

References Cited

The following references, cited by the Examiner, are of record in the patented file of this patent or the original patent.

Chemical Abstracts 54: 1281i (1960).

JEROME D. GOLDBERG, Primary Examiner